United States Patent [19]

Shoesmith

[11] Plant 4,126

[45] Oct. 11, 1977

[54] CHRYSANTHEMUM NAMED LEXINGTON

[75] Inventor: Leonard H. Shoesmith, Westfield-Woking, England

[73] Assignee: Pan-American Plant Company, West Chicago, Ill.

[21] Appl. No.: 733,471

[22] Filed: Oct. 15, 1976

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Rummler and Snow

[57] ABSTRACT

A new and distinct cultivar of chrysanthemum characterized by its single flower form, the clear yellow of its ray florets which do not bronze when finished cool, and flowers which are 3 to 3½ inches in diameter when grown as a spray pot plant. This plant is also distinguished by its vigorous and upright pot habit which is adaptable to cut flower production and by its abundant, deeply serrated dark green foliage.

1 Drawing Figure

BACKGROUND OF THE NEW PLANT

This new variety of chrysanthemum plant originated as a seedling of unidentified parentage and was discovered by me in 1972 among greenhouse plants cultivated by me at Westfield-Woking, Surrey, England, with the object of developing improved chrysanthemum varieties for the commercial market. Asexual reproduction of this new plant was done by me at Westfield-Woking, Surrey, England, by means of cuttings from the original plant and further propagation, by means of vegetative cuttings, carried on at West Chicago, Ill., and at Cortez, Fla., has demonstrated that the distinctive characteristics of this new chrysanthemum plant are firmly fixed and hold true from generation to generation.

DESCRIPTION OF THE DRAWING

My new chrysanthemum plant is illustrated by the accompanying drawings which show the form and color characteristics of the flowers as they appear on a fully grown potted plant and which show the configuration of typical leaves of this new variety by means of pen-and-ink sketches. The color rendition of the floral illustration has been done by conventional photographic procedures and is believed to be as nearly true as it is reasonably possible to obtain, the plant shown having flowered in May 1976.

DESCRIPTION OF THE NEW PLANT

The following is a detailed description of my new variety of chrysanthemum plant according to data obtained by observation of greenhouse plants grown at West Chicago, Ill., and flowered in the months of January, May and August, the color designations being according to The R.H.S. Colour Chart published by the Royal Horticultural Society of London, England.

THE PLANT

Origin: Seedling.

Parentage: Unidentified, this seedling appearing among plants resulting from random crosses.

Classification:

*Botanic.*—*Chrysanthemum morifolium.*

*Commercial.*—Greenhouse pot plant.

Form: Upright, perennial herbaceous bush.

Height: 11 to 15 inches.

Growth: Terminal, upright and vigorous, sturdy, with very good strength.

Foliage: Abundant, six to eight leaves on 4 inches of stem.

*Size of leaf.*—4 to 4½ inches long and 1⅞ to 2½ inches wide for the mature leaf.

*Shape.*—Lobed, deeply serrated.

*Texture.*—Canescent.

*Venation.*—Pinnately veined.

*Color.*—Upper side — Green 139A; Under side — Green 137B.

*Petioles.*—1¼ to 1½ inches long.

THE BUD

Form: Almost global.

Size: Diameter — 7/16 inch; depth — 5/16 inch.

Opening: Slowly

| Color: | Summer | Winter |
|---|---|---|
| When phyllaries first divide: | Yellow 8A | Yellow 10A |
| When florets begin to unfurl: | Yellow 12A | Yellow 12B |

Phyllaries: Many involucral upstanding bracts on outside of the receptacle.

*Shape.*—Spear-shaped.

*Color.*—Inside — Green 138A; Outside — Green 137B.

*Surface texture.*—Pubescent.

Peduncle: Erect and 1¼ to 2¾ inches long.

*Surface texture.*—Pubescent.

THE FLOWER

Response: 10 week.

Recommended flowering: September 15 and June 15 for Northern U.S.A.

Natural flowering season: October 25 to November 2.

Blooms: Flower type — single and composite.

*Borne.*—A head of many ray florets borne on a receptacle.

*Size.*—Medium, 3 to 3½ inches in diameter and ⅝ to ⅞ inch in depth.

*Shape.*—Cup-shaped when bloom first opens and becoming flat when fully opened.

*Florets.*—Numerous ray florets. Form: Linear. Firmness: Medium. Appearance: Very slight shine.

| Color: | January | May | August |
|---|---|---|---|
| Ray florets: | Yellow 3A | Yellow 6A | Yellow 6A |
| Reverse side: | Yellow 5B | Yellow 6C–7B | Yellow 6B |

Discoloration: Very slight fade as full bloom ages.

Penduncle: Sturdy and upright, 1¼ to 2¾ inches long.

*Color.*—Yellow-Green 148B.

Persistence: Flowers hang on and dry.

Lasting quality:

*On plant.*—3 weeks.

*As cut flower.*—7 to 12 days.

REPRODUCTIVE ORGANS

Stamens: Number — 5 syngenesious.

*Filaments.*—1/16 to ⅛ inch long. Color: Light Yellow.

*Pollen.*—Color — Yellow.

Pistils: One to each ray and disc floret.

*Style.*—¼ to 5/16 inch long.

*Stigmas.*—Color — Yellow.

*Ovaries.*—Inferior bicarpellate.

My new chrysanthemum plant is characterized by its single flower form with clear yellow ray florets which do not bronze when finished cool and which do not reflex upon opening but remain in a more-or-less flat or flat-cupped position for the life of the flower. The flower is 3 to 3½ inches in diameter when grown as a spray plant, has a minimal pollen production, and a green coloration of the disc florets prior to attaining maturation.

This new variety is also characterized by its upright pot habit, as opposed to the spreading habit of a Mandalay variety, its abundant dark green foliage, and its ability to be flowered year around when night temperature can be maintained between 60° and 80° F., the plant flowering approximately 10 weeks from the commencement of short day treatment.

I claim:

1. A new and distinct cultivar of chrysanthemum substantially as shown and described, characterized by its single flower form with clear yellow ray florets which do not bronze when finished cool and which do not reflex upon opening, by its upright pot habit, and by its abundant production of dark green foliage.

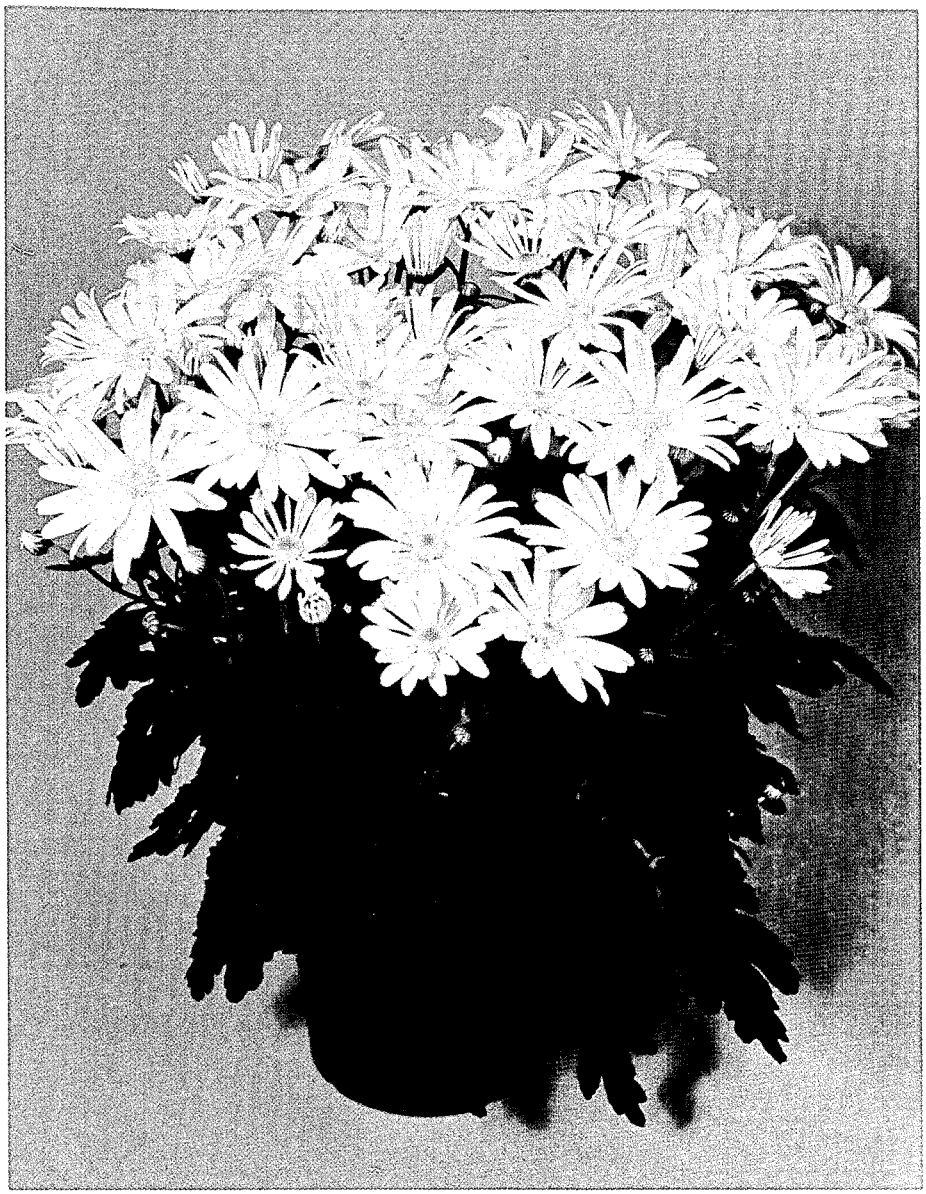
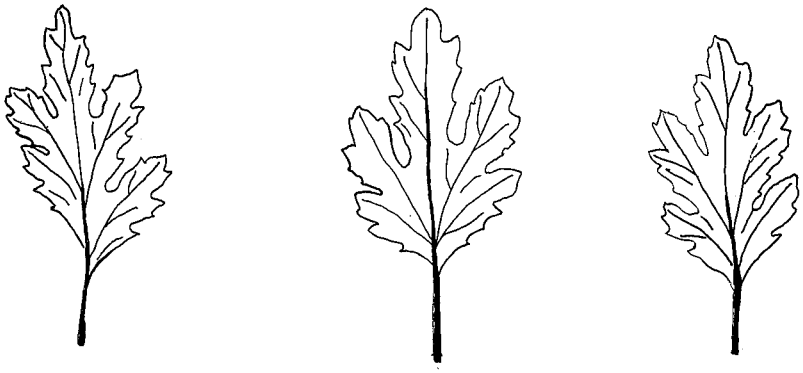

* * * * *